United States Patent [19]

Parins et al.

[11] Patent Number: 5,201,732
[45] Date of Patent: Apr. 13, 1993

[54] BIPOLAR SPHINCTEROTOMY UTILIZING SIDE-BY-SIDE PARALLEL WIRES

[75] Inventors: David J. Parins, Corcoran; Michael J. Hollenhorst, Brainerd, both of Minn.

[73] Assignee: Everest Medical Corporation, Minneapolis, Minn.

[21] Appl. No.: 866,320

[22] Filed: Apr. 9, 1992

[51] Int. Cl.⁵ ............................................ A61B 17/39
[52] U.S. Cl. ........................................ 606/47; 606/48
[58] Field of Search .......................... 606/47, 48, 50

[56] References Cited

U.S. PATENT DOCUMENTS

| | | |
|---|---|---|
| 164,184 | 6/1875 | Kidder . |
| 3,910,279 | 10/1975 | Okada et al. ............... 606/47 |
| 4,181,131 | 1/1980 | Ogiu . |
| 4,202,337 | 5/1980 | Hren et al. . |
| 4,325,374 | 4/1982 | Komiya . |
| 4,493,320 | 1/1985 | Treat . |
| 4,905,691 | 3/1990 | Rydell . |
| 4,919,133 | 4/1990 | Chiang . |
| 5,035,696 | 7/1991 | Rydell . |

*Primary Examiner*—Lee S. Cohen
*Attorney, Agent, or Firm*—Haugen and Nikolai

[57] ABSTRACT

A bipolar sphincterotomy for use in endoscopic retrograde sphincterotomy procedures includes an elongated, flexible, plastic tube having either a single or a double lumen extending between its distal and proximal ends. At least one, but preferably two, aperture(s) is formed through the wall of the plastic tubular member a predetermined distance proximal of the distal end of the plastic tubular member. A pair of conductive wires extend through the lumen from the proximal end and exit the lumen through the aperture(s). The distal ends of pair of wires are mechanically joined to the tube so that the portions of the wires extending exteriorly of the lumen are in parallel, spaced relation with a predetermined gap therebetween. The exposed portions of the wires comprise a bipolar pair of electrodes. At least one of the wires is free to move longitudinally within the lumen of the tubular member to bow the tubular member in the location between the aperture and the points of attachment of the pair of wires to the tubular member when a pulling force is applied to one or both of the wires at the proximal end of the tubular member.

8 Claims, 2 Drawing Sheets

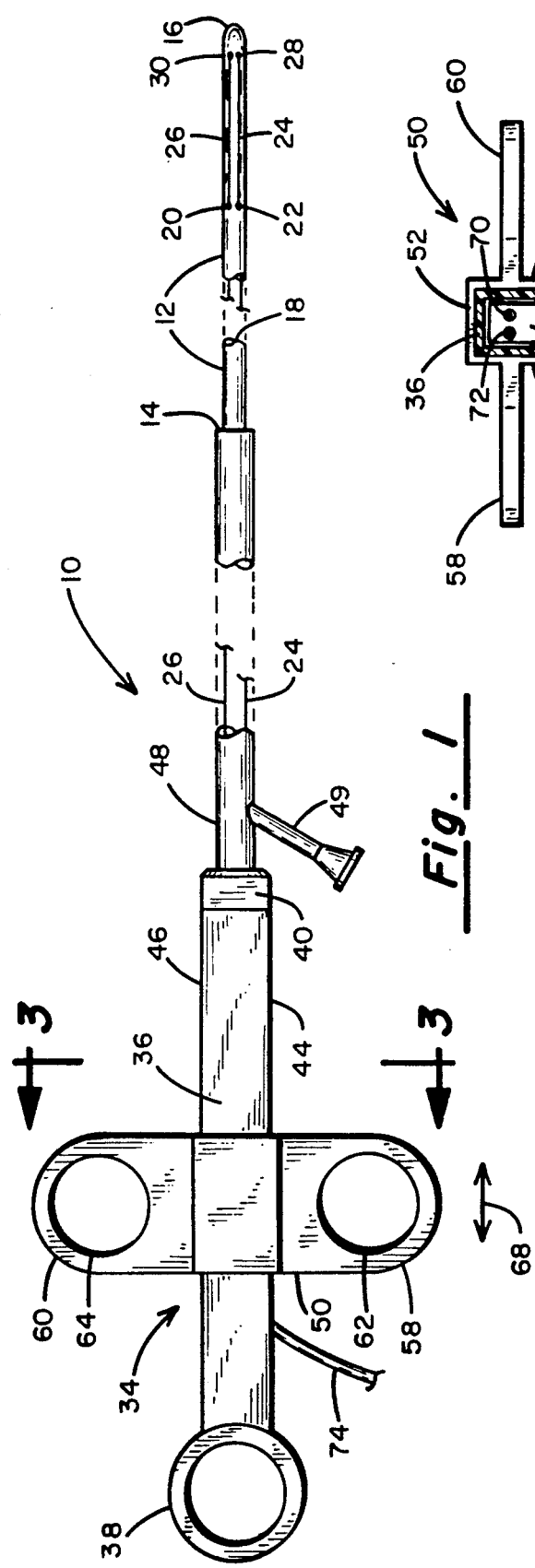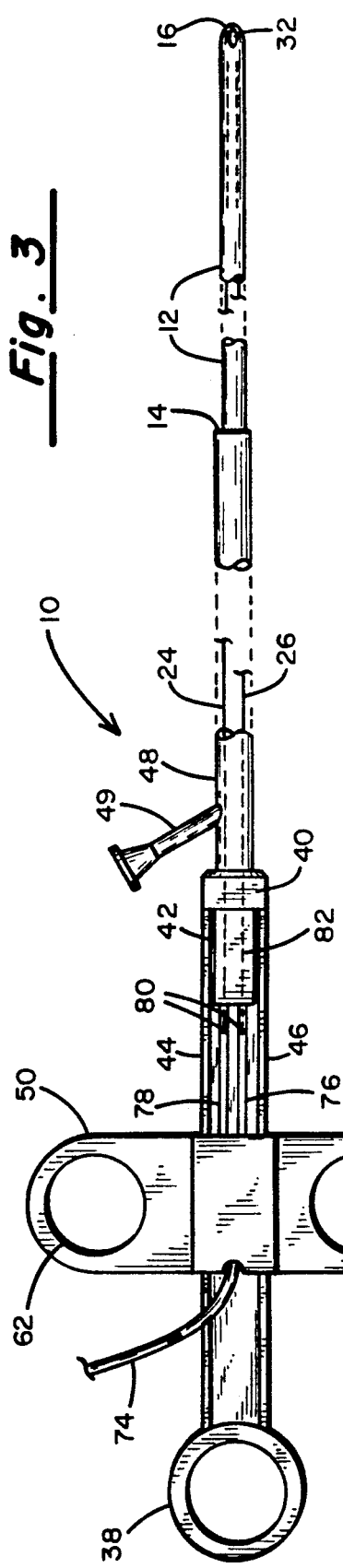

BIPOLAR SPHINCTEROTOMY UTILIZING SIDE-BY-SIDE PARALLEL WIRES

BACKGROUND OF THE INVENTION

I. Field of the Invention

This invention relates generally to electrosurgical apparatus, and more particularly to a catheter-based bipolar electrosurgical device which can be passed through an endoscope into the duodenum to the site of the papilla of Vater and which can be deployed to cut the sphincter of Oddi to allow passage of gallstones from the common bile duct in the duodenum.

II. Discussion of the Prior Art

As is set in the "Discussion of the Prior Art" of U.S. Pat. No. 5,035,696 to Rydell, when gallstones form in the gallbladder and achieve a size too large to pass through the cystic duct and the common bile duct into the duodenum, a gallbladder attack may result leading to intense pain and possible surgical removal of the gallbladder itself. Where the site of the blockage is the sphincter of Oddi, a less traumatic procedure referred to as "endoscopic retrograde sphincterotomy" (ERS) may be used to cut the sphincter sufficiently to permit even large size gallstones to pass into the duodenum. In carrying out the ERS procedure, a side-viewing endoscope is passed through the esophagus into the stomach and from there through the pyloric sphincter into the duodenum. Using a fiber optic bundle, the distal end of the endoscope is made to approach the papilla of Vater and, when so positioned, a cannula is passed through the endoscope and through the sphincter of Oddi into the common bile duct. At this point, a contrast fluid may be injected so that any gallstones can be viewed fluoroscopically and their size evaluated. If a stone is deemed to be too large to pass through the sphincter of Oddi even when enlarged, the sphincterotomy procedure is terminated and the patient at that point becomes an abdominal surgery candidate. However, if the size of the gallstones are sufficiently small, an electrosurgical instrument referred to as a sphincterotomy or papillotome is made to pass through a side port in the endoscope and through the sphincter of Oddi. At this point, the instrument is used to cut the sphincter of Oddi to effectively allow it to expand and pass gallstones of a size too large to pass through that sphincter normally.

Electrosurgical sphincterotomies of the prior art have been monopolar in nature. In particular, it would typically comprise an elongated tube having a proximal end, a distal end and a lumen extending between the two ends. A small aperture is formed a short distance proximal of the distal end and a conductive wire is routed through the lumen of the tube, out the aperture and then anchored proximate the distal tip of the tube. This wire would be electrically coupled to an electrosurgical generator whose other terminal connects to an indifferent electrode called a patient plate placed in electrical contact with the patient's buttocks. By applying a tension force to the proximal end of the aforementioned wire following its placement through the sphincter of Oddi, the tip portion of the sphincterotomy becomes bowed and when the voltage is applied between the wire and the patient plate, a current flows from the wire through contacting tissue and from there through a path of least resistance to the patient plate. This type of monopolar sphincterotomy is more particularly described in Demling et al. German Offenlegungsschrift 24 26 781.

The use of a monopolar sphincterotomy has led to a number of problems, chiefly due to the unpredictable nature of the current return path through the body to the patient plate. Where conductive fluids have been introduced into the common bile duct at the outset to assess stone sizes, that fluid also finds its way into the pancreatic duct which is directly adjacent the sphincter of Oddi. Recognizing that the contrast fluid is a highly conductive liquid, one path of least resistance from the monopolar cutting wire to the patient plate is through pancreatic tissue. This current flow has been found to raise the temperature of the pancreas to the point where cells become inflamed, leading to a serious condition called "pancreatitis". It is also found the depth of tissue destruction resulting from a monopolar electrosurgical sphincterotomy may be excessive and in some instances, this has led to a perforation of the bowel. In this event, the patient must undergo abdominal surgery to correct that condition.

In that the site of the sphincter of Oddi is highly vascularized, considerable bleeding takes place during a ERS procedure, especially where a monopolar electrosurgical sphincterotomy is employed.

SUMMARY OF THE INVENTION

Most of the foregoing problems are obviated through the use of the sphincterotomy of the present invention. Rather than being monopolar in nature, the present invention comprises a bipolar sphincterotomy.

The device of the present invention differs from that disclosed in the Rydell U.S. Pat. No. 5,035,696 in that rather than employing a uninsulated wire segment as the active electrode and a larger area flexible conductive member as the indifferent electrode, in accordance with the present invention, the bipolar electrodes comprise a pair of conductive wire segments that run side-by-side along a portion of an elongated flexible plastic tubular sheath in a region near its distal end. More particularly, the device, in accordance with this invention, comprises an elongated, flexible tubular catheter body with a proximal end, a distal end and at least one lumen extending the length of the catheter. Near the distal end of the catheter, but a predetermined distance proximal thereof, is at least one, but preferably two apertures which extends through the side wall of the tube. Passing through the lumen from the proximal end are a pair of conductors which remain insulated from one another over the length of the tube and which individually exit through the aperture(s) and then extend along the outer surface of the catheter to a point where they are mechanically joined to the catheter near its distal end. The externally disposed wire segments extend parallel to one another and are free of insulation and thereby create a bipolar electrode pair.

Located at the proximal end of the tubular catheter is a handle member having a finger-operated slide coupled to at least one of the conductors whose distal end portions pass through the aperture(s) in the catheter body. By manipulating the slide, the distal end portion of the catheter disposed between the apertures and the point of attachment of the wires to the catheter body may be made to bow. The exposed portions of the two wires that run side by side exterior to the catheter body form a bipolar electrode pair. When the distal end portion of the catheter is fitted through the sphincter of Oddi and a high frequency voltage is applied across the two wires, the resulting current path is localized to the tissue present between the exposed portions of the two wires As with the arrangement described in the Rydell U.S. Pat. No. 5,035,696, the present invention also permits better control over the depth of tissue destruction than can be achieved using a monopolar sphincterotomy of the type described in the aforereferenced Demling et al. German Offenlegungsschrift.

DESCRIPTION OF THE DRAWINGS

The foregoing objects, features and advantages of the invention will become more apparent to those skilled in the art from the following detailed description of various embodiments of the invention in which like numerals in the several views refer to corresponding parts.

FIG. 1 is a top view of the sphincterotomy apparatus of the present invention;

FIG. 2 is a bottom view of the apparatus of FIG. 1;

FIG. 3 is a cross-sectional view of the apparatus of FIG. 1 taken along the section line 3—3 in FIG. 1;

DESCRIPTION OF THE PREFERRED EMBODIMENTS

Figure 4:
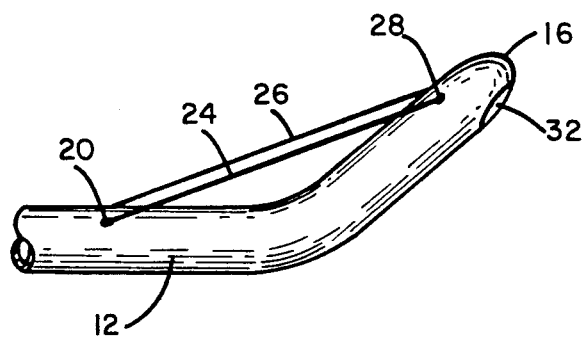
FIG. 4 is an enlarged partial view of the distal portion of the sphincterotomy device of FIG. 1 when in its cutting position.

Referring first to FIG. 1, there is indicated generally by numeral 10 a bipolar sphincterotomy to be used during an endoscopic retrograde sphincterotomy to enlarge the opening surrounded by the sphincter of Oddi so that gallstones of a predetermined size or less may more readily pass from the common bile duct into the duodenum. The instrument is seen to comprise an elongated flexible tubular member 12 having a proximal end 14 and a distal end 16 with either one or two lumens 18 extending between the two ends of the tube 12. Located a predetermined distance proximal of the distal end 16 of the tube 12 and extending through the wall thickness of the tube are first and second radially spaced apertures 20 and 22. Disposed within the lumen(s) 18 are a pair of conductive wires 24 and 26 which may be covered with a coating of insulation to prevent electrical shorting therebetween as they extend through the lumen 18 of the tubular member. By using a double lumen tube, the need for a coating of insulation on the individual wires is obviated.

With reference again to FIGS. 1 and 2, the distal end portions of the wires 24 and 26 (preferably stainless steel) extend through the apertures 22 and 20, respectively, and then are mechanically anchored to the plastic tubular member 12 at 28 and 30. The portions of the wires 24 and 26 extending exterior to the lumen 18 are free of the insulating coating and thereby form bipolar electrode surfaces.

Located at the proximal end of the bipolar sphincterotomy 10 is a handle member, indicated generally by numeral 34. It comprises an elongated channel 36 of generally rectangular crosssection as best seen in FIG. 3. The channel 36 terminates at its proximal end in an integrally molded thumb ring 38. The distal end of the channel member 36 includes a nose cap 40 which includes a stem portion 42 which is dimensioned to fit between the side walls 44 and 46 of the channel member 36. The end cap 40 has a longitudinal bore formed therein into which is inserted a relatively short length of plastic tubing 48. It coaxially surrounds the elongated tubular member 12 and thus acts to reinforce the coupling between the tube 12 and the handle member 34. Extending laterally outward from the tube 48 is a Y-connection 49 equipped with a Luer fitting. The Y-connector is in fluid communication with the lumen of tube 12, allowing a fluid, such as a contrast medium or a flushing liquid to be perfused out the distal port 32 of the instrument.

A slide member 50 is operatively coupled to the elongated channel 36. With reference to FIG. 3, it is seen to include a tubular portion 52 of generally rectangular cross-section and extending laterally from opposite side surfaces 54 and 56 thereof are wings 58 and 60, each of which is provided with an enlarged aperture 62 and 64 for receiving the forefinger and index finger of the surgeon's hand when his or her thumb is inserted in the thumb ring 38. Affixed to the bottom surface 64 of the tubular segment 52 is a slide block 66 whose dimensions are such that there is a somewhat loose fit between the slide member 50 and the elongated channel 36, allowing reciprocal movement of the slide in the direction indicated by the double-headed arrow 68 in FIG. 1. Referring now to the bottom view of FIG. 2 and the crosssectional view of FIG. 3, the slide block 66 has parallel bores 70 and 72 formed lengthwise therethrough and into which are fitted from their proximal) end the conductors of a power cord 74 and from their opposite end first and second stainless steel tubes 76 and 78. The conductors of the power cord 74 actually fit into the central lumens of the stainless steel tubes 76 and 78 and are held in place by crimping or pinching the stainless steel tubes as at points 80, thus insuring good electrical contact and a strong mechanical connection between the power cord 74 and the conductors 24 and 26 which also are inserted into the lumens of the stainless steel tubes 76 and 78. As is further evident from FIG. 2, the stainless steel tubes 76 and 78 extend through a molded plastic guide 82 affixed to the nose cap 40 and into the lumen of the reinforcing plastic tubular member 48. The power cord 74 is provided with a plug (not shown) allowing it to interface with an electrosurgical generator suitable for use with the sphincterotomy of the present invention. It may be of the type described in the Stasz et al. U.S. Pat. No. 4,903,696, and entitled "Electrosurgical Generator" and assigned to the assignee of the present invention.

FIG. 4 is an illustration of the distal end portion of the sphincterotomy of FIG. 1 when the slide 50 is pulled in the proximal direction to apply a tension force on the conductors 24 and 26. The portion of the tube 12 between the apertures 20, 22 and the connection points 28, 30 being flexible, allows the instrument to bow in the manner shown.

Figure 5:
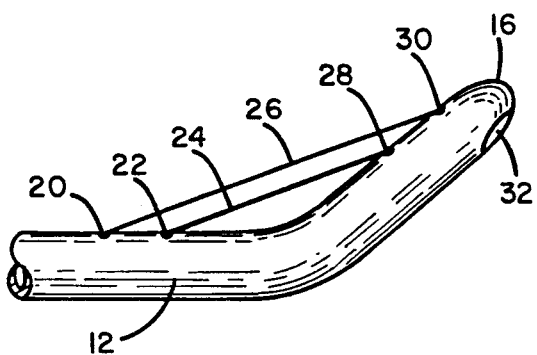
FIG. 5 is a fragmentary view of a portion of the tubular catheter utilizing a bilumen construction.
Figure 6:
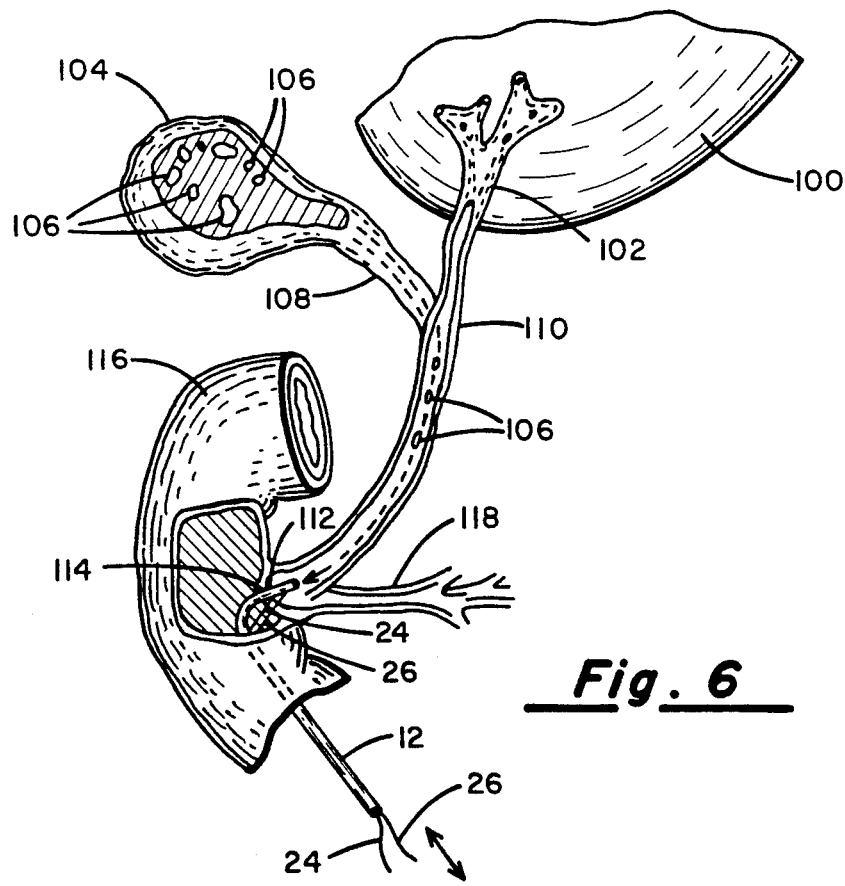
FIG. 6 is an anatomical diagram of the accessory organs of the digestive tract helpful in illustrating the use of the sphincterotomy of the present invention.

The embodiment illustrated in FIG. 5 is identical in all respects to the previously described embodiment, save for one modification. Rather than having the apertures 20 and 22 radially separated from each other as described above, in the arrangement of FIG. 5, those apertures are longitudinally spaced a short predetermined distance apart allowing the electrode portions of the wires 24 and 26 exiting therefrom to lie in a common generally vertical plane before attaching to the exterior wall of the tube 12 at points 28 and 30 which are also then longitudinally spaced from each other.

Having described the preferred embodiments of the sphincterotomy comprising the present invention, attention will next be given to its mode of use and, in that regard, reference will also be had to the anatomical diagram illustrated in FIG. 5. In this diagram, the liver is identified by numeral 100 and the hepatic duct by numeral 102. The gallbladder is identified by numeral 104 and is sectioned to reveal a number of gallstones as at 106, the stones varying in both size and shape. The cystic duct 108 connects the gallbladder 104 to the common bile duct, which is also sectioned open to reveal the presence of further stones 106 therein.

The common bile duct leads to the sphincter of Oddi 112 located at the duodenal papilla 114 sometimes referred to as the papilla Vater. The duodenum is identified by numeral 116 and the pancreatic duct by numeral 118.

When gallstones form because of an excess of cholesterol in the bile and/or the absorption of too much bile acids from the bile, they may pass from the gallbladder and down the common bile duct into the duodenum without problem provided the stones are sufficiently small. Occasionally, however, the gallstones within the gallbladder develop to a size where they may block the normal flow of bile during digestion of fatty foods, resulting in a blockage of the cystic duct 108 or the common bile duct 110. The sphincter of Oddi comprises a restriction and is a location where a larger stone may not be able to pass. In the ERCP procedure, a side viewing endoscope is inserted down the patient's esophagus through the stomach and into the duodenum. While viewing the surgical site through a fiber optic rod, the surgeon may first pass a small diameter cannula through a side port of the endoscope to gently lift the tissue flap covering the papilla of Vater at 114 and then it is advanced into the common bile duct. A suitable contrast fluid, such as Hypaque® meglumine 60%, may then be injected through the cannula whereby the condition of the common bile duct and the stone content thereof can be assessed. Subsequently, the elongated tube portion 12 of the sphincterotomy 10 is routed through the endoscope and the tapered distal tip 16 is advanced through the sphincter. (In FIG. 5, the endoscope is not shown so that the sphincterotomy of the present invention can better be viewed.) At this time, the tension on the cutting wires 24 and 26 is nil and the distal end portion of the sphincterotomy remains substantially rectilinear. With the distal end portion of the sphincterotomy so positioned, the surgeon may next pull back with his thumb in the proximal direction on the slide 50 and, in doing so, will apply a tensioning force to the cutting wires 24 and 26 causing the distal end portion to bow as illustrated in FIG. 4. When so positioned, the surgeon depresses a foot switch (not shown) causing the RF voltage provided by the electrosurgical generator to be applied between the cutting wires 24 and 26 which form a bipolar electrode pair. In that the tissue comprising the sphincter of Oddi will at this time be in contact with the wires 24 and 26, the tissue will be cut at its locations between the points of contact with the wires 24 and 26 to thereby enlarge the opening defined by the sphincter of Oddi. At this point, substantially larger stones than could normally pass will find their way out through the enlarged sphincter into the duodenum and will then pass through the remainder of the digestive tract.

By utilizing an appropriate power setting on the electrosurgical generator, e.g., the blend mode discussed in the aforereferenced Stasz et al patent application, the cutting is accompanied by coagulation, thereby significantly reducing the loss of blood. Moreover, because the electrode configuration is bipolar, the current path is only through tissue between the cutting wires 24 and 26. Hence, the tendency for substantial electrical currents to flow through the conductive contrast fluid or other body fluids contained in the pancreatic duct is eliminated and the likelihood of a subsequent inflammation of the pancreas often accompanying monopolar sphincterotomy is markedly reduced.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A bipolar electrosurgical instrument for performing a sphincterotomy comprising:
 (a) an elongated, flexible, plastic, tubular member of a predetermined diameter about a longitudinal axis having a proximal end, a distal end and at least one lumen extending between said proximal end and said distal end, said tubular member normally being rectilinear and including a pair of apertures extending through its wall into said lumen at a predetermined distance proximal of said distal end; and
 (b) a pair of conductive wires extending through said lumen from said proximal end and out through said apertures, said wires having distal ends attached to said tubular member proximate said distal end of said tubular member, said pair of wires being electrically insulated from one another along the length of said lumen and extending parallel, spaced relation and being free of insulation between said apertures and the attachment point to said tubular member to form bipolar electrodes, at least one of said pair of wires being free to move longitudinally within said lumen to bow said tubular member in the location between said apertures and the points of attachment of said pair of wires to said tubular member when a pulling force is applied to said one of said pair of wires at said proximal end of said tubular member.

2. An electrosurgical instrument as in claim 1 wherein said pair of apertures are longitudinally separated, allowing said bipolar electrodes to reside in a common plane which includes said longitudinal axis of said tubular member.

3. An electrosurgical instrument as in claim 1 wherein said pair of apertures are radially separated, allowing said bipolar electrodes to reside in a common plane which is non-coplanar with said longitudinal axis of said tubular member.

4. The electrosurgical instrument as in claim 3 wherein said pair of apertures are radially spaced from one another at the same predetermined distance proximal of said distal end of said tubular member.

5. The electrosurgical instrument as in claim 1 and further including a plastic handle attached to said proximal end of said tubular member, said handle including a longitudinally movable slide member coupled to said one of said wires for applying said pulling force.

6. The electrosurgical instrument as in claim 5 and further including means in fluid communication with said lumen for introducing one of a contrast and flushing liquid into said lumen.

7. The electrosurgical instrument as in claim 1 wherein said pair of wires each include an insulating jacket surrounding the portion thereof contained within said lumen and being mechanically and not electrically joined to each other within said lumen.

8. The electrosurgical instrument as in claim 1 wherein said tubular member includes two lumens separately containing said pair of wires.

* * * * *

UNITED STATES PATENT AND TRADEMARK OFFICE
CERTIFICATE OF CORRECTION

PATENT NO. :  5,201,732
DATED      :  April 13, 1993
INVENTOR(S):  David J. Parins and Michael J. Hollenhorst It is certified that error appears in the above-identified patent and that said Letters Patent is hereby corrected as shown below:

Claim 1, column 6, line 40, after "and extending" insert -- in --.

Signed and Sealed this

Twenty-eighth Day of December, 1993

Attest:

BRUCE LEHMAN

*Attesting Officer*       *Commissioner of Patents and Trademarks*